United States Patent [19]

Mills

[11] Patent Number: 5,997,901

[45] Date of Patent: Dec. 7, 1999

[54] METHOD OF MANUFACTURING SCENTED MOLDED PRODUCTS

[76] Inventor: Robert G. Mills, 202 - 5677 - 208th St., Langley, British Columbia, Canada, V3A 4N4

[21] Appl. No.: 09/176,746

[22] Filed: Oct. 22, 1998

[51] Int. Cl.$^6$ .............................. A61K 9/20; A61K 9/46; A61K 9/14; A61K 9/00

[52] U.S. Cl. .................. 424/464; 424/466; 424/715; 424/717; 424/660; 424/400; 424/484; 512/5

[58] Field of Search ..................... 424/464, 484, 424/400, 466, 715, 717, 660; 512/5; 510/130, 141, 446, 445, 447, 440, 509, 451

[56] References Cited

U.S. PATENT DOCUMENTS

| | | | |
|---|---|---|---|
| Re. 33,086 | 10/1989 | Bru | 424/44 |
| 4,929,378 | 5/1990 | Morita et al. | 252/106 |
| 4,968,517 | 11/1990 | Gergely et al. | 426/285 |
| 5,110,603 | 5/1992 | Rau | 424/44 |
| 5,516,529 | 5/1996 | Zellweger | 424/466 |

OTHER PUBLICATIONS

Micheels, Carolyn J. (AN 1999:115255 Promt, abstract of Soap and Cosmetics, (Jan. 1999), vol. 75, No. 1, pp. 46(1).

*Primary Examiner*—S. Mark Clardy
*Assistant Examiner*—Sabiha N. Qazi
*Attorney, Agent, or Firm*—Oyen Wiggs Green & Mutala

[57] ABSTRACT

A scented molded product, e.g. an effervescent bath tablet or an air freshener, is made by mixing sodium bicarbonate, water and fragrance oils to form a first mixture, adding to this first mixture a citric acid mixture comprising sodium borate mixed with citric acid to form a third mixture and molding and drying the third mixture to form a hardened product.

11 Claims, No Drawings

METHOD OF MANUFACTURING SCENTED MOLDED PRODUCTS

BACKGROUND OF THE INVENTION

1. Field of the Invention

The present invention relates to a method of manufacturing scented molded products and is useful, in particular, for the manufacture of effervescent bath tablets and air fresheners.

2. Description of the Related Art

Conventionally, effervescent bath tablets are made by molding components together under pressure, using as one of the components a volatile ingredient, such as isopropyl alcohol or products such as propylene glycol or oils such as canola or almond, as a binding agent.

The present invention is based on appreciation of the fact that it is preferable to avoid the use of volatile ingredients and/or other chemical but not natural substances or sticky substances such as oils and to effect a binding together of the components of the tablets by means of a chemical binding process, rather than by pressure.

BRIEF SUMMARY OF THE INVENTION

According to the present invention, a method of manufacturing scented tablets comprises the steps of mixing sodium bicarbonate, water and fragrance oils to form a first mixture, mixing sodium borate and citric acid to form a citric acid mixture, mixing together the first mixture and the citric acid mixture to form a third mixture, molding the third mixture to form the tablets and drying the tablets to a hardened condition, e.g. by evaporation or by the application of heat. An initial mild chemical reaction causes the sodium bicarbonate and the citric acid to bind together chemically.

It has been found that satisfactory results can be obtained by employing 790 to 900 parts by weight of sodium bicarbonate, 10 to 25 parts by weight of water, 3 to 8 parts by weight of fragrance oils and 260 to 300 parts by weight of the citric acid mixture and by employing, for the citric acid mixture, 15 to 18 parts by weight of sodium borate and 312 to 343 parts by weight of solid citric acid, preferably in the form of 117 to 130 parts by weight of citric acid powder and 195 to 213 parts by weight of citric acid granules.

The sodium bicarbonate, water and fragrance oils are mixed together for a period sufficient to moisten the sodium bicarbonate and allow the sodium bicarbonate to subsequently absorb the citric acid mixture, and it has been found that a period of four minutes is suitable for this purpose. The citric acid mixture is added slowly to the first mixture, while being mixed with the first mixture, over a period of approximately ten seconds and the resulting third mixture is then further mixed for a period of 37 to 40 seconds, depending upon the humidity of the surrounding air.

The invention will be more readily understood from the following description of an example.

EXAMPLE

An amount of 900 g of sodium bicarbonate is placed into a mixing bowl, and is then mixed in the mixing bowl with 12 g of water and 3 g of fragrance oils for a period of approximately four minutes. This causes the sodium bicarbonate to become moistened and allows subsequent absorption of a citric acid mixture.

After mixing this first mixture for a period of four minutes, 300 g of citric acid mixture is added. The citric acid mixture is formulated from 18 g of sodium borate, 130 g of citric acid powder and 213 g of citric acid granules. This citric acid mixture is mixed slowly, for a period of approximately four seconds, into the first mixture in the mixing bowl and, when all the citric acid mixture has been added to the bowl, the mixing is maintained for a further period of 37 to 40 seconds, depending on the humidity of the surrounding air. The resulting third mixture is then packed into tablet molds using only enough pressure to form the required tablet shapes. Once the shapes have been formed in the molds, the tablets are released from the molds and are then dried by evaporation or by heating. By this process, there is produced an initial mild chemical reaction by which the sodium bicarbonate and the citric acid bind together chemically. The tablets are dried natural by evaporation over a period of 4 to 8 hours or, by the application of a combination of air flow and heat, over a shorter period, so that the chemical reaction is terminated within about 10 to 15 minutes. The resulting products are hard and durable, provided that the mixtures have been properly mixed.

I claim:

1. A method of manufacturing scented molded product which comprises the steps of mixing sodium bicarbonate, water and fragrance oils to form a first mixture; mixing sodium borate and citric acid to form a citric acid mixture; mixing together said first mixture and said citric acid mixture to form a third mixture; molding said third mixture to form said product and drying the product to a hardened condition.

2. A method as claimed in claim 1, wherein the step of forming said citric acid mixture comprises adding said citric acid in a dry form to said sodium borate.

3. A method as claimed in claim 2, wherein the step of forming said citric acid mixture comprises employing citric acid powder and citric acid granules as said citric acid.

4. A method as claimed in claim 1, in which the step of mixing said first mixture with said citric acid mixture is continued for a period of time sufficient to cause said sodium bicarbonate and said citric acid to bind together.

5. A method of manufacturing scented molded product, comprising the steps of mixing 790 to 900 parts by weight of sodium bicarbonate, 10 to 25 parts by weight of water and 3 to 8 parts by weight of fragrance oils sufficiently to moisten said sodium bicarbonate and to form a first mixture; mixing 15 to 18 parts by weight of sodium borate and 312 to 343 parts by weight of solid citric acid to form a citric acid mixture; adding 260 to 300 parts by weight of said citric acid mixture to said first mixture to form a third mixture; molding said third mixture to form a molded product and drying said molded product to a hardened condition.

6. A method as claimed in claim 5, wherein the step of mixing said citric acid mixture is effected for a duration of only approximately 10 seconds.

7. A method as claimed in claim 5, wherein the step of mixing said first mixture and said citric acid mixture is effected for a duration of approximately 37 to 40 seconds.

8. A method as claimed in claim 5, wherein said solid citric acid comprises 117 to 130 parts by weight of citric acid powder and 195 to 213 parts by weight of citric acid granules.

9. A method as claimed in claim 5, wherein said first mixture comprises approximately 900 parts by weight of sodium bicarbonate, 12 parts by weight of water and 3 parts by weight of fragrance oils, the amount of said citric acid mixture is approximately 300 parts by weight and said citric acid mixture comprises approximately 18 parts by weight of sodium borate, 130 parts by weight of citric acid powder and 213 parts by weight of citric acid granules.

10. A method as claimed in claim 9 wherein the step of mixing said citric acid mixture is effected for a duration of only approximately 10 seconds.

11. A method as claimed in claim 10, wherein the step of mixing said first mixture and said citric acid mixture is effected for a duration of approximately 37 to 40 seconds.

* * * * *